United States Patent
Masuda

(10) Patent No.: US 10,444,200 B2
(45) Date of Patent: Oct. 15, 2019

(54) IMAGE GENERATION APPARATUS AND IMAGE GENERATION METHOD

(71) Applicant: Seiko Epson Corporation, Tokyo (JP)

(72) Inventor: Hiroyuki Masuda, Chino (JP)

(73) Assignee: Seiko Epson Corporation (JP)

( * ) Notice: Subject to any disclaimer, the term of this patent is extended or adjusted under 35 U.S.C. 154(b) by 204 days.

(21) Appl. No.: 15/456,897

(22) Filed: Mar. 13, 2017

(65) Prior Publication Data

US 2017/0269040 A1    Sep. 21, 2017

(30) Foreign Application Priority Data

Mar. 18, 2016 (JP) ................. 2016-054944

(51) Int. Cl.
*G01N 29/34* (2006.01)
*G01N 29/44* (2006.01)
*G01S 7/52* (2006.01)
*G01S 15/89* (2006.01)

(52) U.S. Cl.
CPC ....... *G01N 29/348* (2013.01); *G01N 29/4463* (2013.01); *G01S 7/52038* (2013.01); *G01S 7/52047* (2013.01); *G01N 29/34* (2013.01); *G01N 29/44* (2013.01); *G01S 15/8977* (2013.01)

(58) Field of Classification Search
CPC ...... G01N 29/34; G01N 29/348; G01N 29/44; G01N 29/4463; G01S 7/52038; G01S 7/52047; G01S 15/8977; G01S 15/8915; G01S 15/8993
See application file for complete search history.

(56) References Cited

U.S. PATENT DOCUMENTS

| 6,937,189 B2* | 8/2005 | Kim | H04B 7/0408 342/372 |
| 2014/0121516 A1* | 5/2014 | Kim | G01S 7/52047 600/437 |
| 2014/0198621 A1* | 7/2014 | Kim | B06B 1/0633 367/138 |

(Continued)

FOREIGN PATENT DOCUMENTS

| EP | 2 815 701 A1 | 12/2014 |
| JP | 2015-071028 A | 4/2015 |
| JP | 2016-086875 A | 5/2016 |

OTHER PUBLICATIONS

Extended European Search Report for Application No. EP 17 16 1315 dated Aug. 3, 2017 (10 pages).

(Continued)

*Primary Examiner* — Natalie Huls
(74) *Attorney, Agent, or Firm* — Harness, Dickey & Pierce, P.L.C.

(57) ABSTRACT

An image generation apparatus including a computation processing section that generates an ultrasonic image from a received signal associated with each scanning of an object in which an ultrasonic wave is transmitted and received is provided. The computation processing section sets, for each scanning, a selection range over which the received signal is received and which includes the direction of the scanning, calculates weights used in a beamforming process based on the received signals within the selection range, and carries out the beamforming process based on the weights to generate an image associated with the scanning.

8 Claims, 12 Drawing Sheets

(56) References Cited

U.S. PATENT DOCUMENTS

| | | | |
|---|---|---|---|
| 2015/0016226 A1* | 1/2015 | Kim | G01S 7/52047 |
| | | | 367/138 |
| 2015/0063058 A1 | 3/2015 | Watanabe et al. | |
| 2015/0073277 A1* | 3/2015 | Hayashi | G01S 7/52038 |
| | | | 600/447 |
| 2015/0293215 A1* | 10/2015 | Kim | G01S 15/8993 |
| | | | 367/7 |
| 2016/0054435 A1* | 2/2016 | Kim | G01S 7/52047 |
| | | | 367/7 |
| 2016/0124082 A1 | 5/2016 | Masuda | |
| 2016/0228092 A1* | 8/2016 | Kim | A61B 8/4427 |
| 2017/0311928 A1* | 11/2017 | Jeon | A61B 8/461 |

OTHER PUBLICATIONS

Synnevåg et al., "Benefits of Minimum Variance Beamforming in Medical Ultrasound Imaging", IEEE Transactions on Ultrasonics, Ferroelectrics, and Frequency Control, vol. 56, No. 9, pp. 1868-1879 (Sep. 2009).

Jensen et al., "An Approach to Multibeam Covariance Matrices for Adaptive Beamforming in Ultrasonography", IEEE Transactions on Ultrasonics, Ferroelectrics, and Frequency Control, vol. 59, No. 6, pp. 1139-1148 (Jun. 2012).

* cited by examiner

| SIMULATION CONDITION | | (1) | (2) |
|---|---|---|---|
| DRIVE CONDITION | TRANSMISSION FREQUENCY | 5.0 MHz | 2.5 MHz |
| | OPENING WIDTH | 19.2 mm | 19.2 mm |
| | SCAN ANGLE INTERVAL | 0.05 ° | 0.05 ° |
| OBSERVATION DEPTH | | 50 mm | 100 mm |
| OBJECT UNDER OBSERVATION (SCATTERERS) | | 0.5-mm-INTERVAL | 3-mm-INTERVAL |

| DRIVE CONDITION | TRANSMISSION FREQUENCY | 2.6 MHz |
|---|---|---|
| | OPENING WIDTH | 38.4 mm |
| | SCAN ANGLE INTERVAL | 0.1° |

IMAGE GENERATION APPARATUS AND IMAGE GENERATION METHOD

BACKGROUND

1. Technical Field

The present invention relates to an image generation apparatus and image generation method for generating an ultrasonic image.

2. Related Art

A known image generation apparatus scans an object with an ultrasonic beam by use of a probe having a plurality of ultrasonic elements (ultrasonic vibrators) to generate an image of the interior of a living body. To generate an image, a beamforming process of transmitting an ultrasonic wave from a body surface of a subject toward the interior of the living body and summing signals that each carry a received reflected ultrasonic wave is carried out. However, since a simple beamforming process only allows generation of a low-resolution image, a technology for obtaining a higher-resolution image has been developed. An example of this technology is the MVB (minimum variance beamforming) process described in JP-A-2015-71028.

According to related art represented by the MVB process, a certain-level resolution is provided. As for an ultrasonic image, however, the higher the resolution, the better the image. If the resolution of an ultrasonic image can be increased with no increase in the number of ultrasonic elements or the frequency at which the ultrasonic elements are driven, everything works out as desired.

SUMMARY

An advantage of some aspects of the invention is a novel approach to a beamforming process capable of achieving higher resolution.

A first aspect of the invention is directed to an image generation apparatus including a computation processing section that generates an ultrasonic image from a received signal associated with each scanning in which an ultrasonic wave is transmitted and received, and the computation processing section sets, for each scanning, a selection range over which the received signal is received and which includes a direction of the scanning, calculates weights used in a beamforming process based on the received signals within the selection range, and carries out the beamforming process based on the weights to generate an image associated with the scanning.

As another aspect of the invention, the invention may be configured as an image generation method for generating an ultrasonic image from a received signal associated with each scanning in which an ultrasonic wave is transmitted and received, the method including setting, for each scanning, a selection range over which the received signal is received and which includes a direction of the scanning, calculating weights used in a beamforming process based on the received signals within the selection range, and carrying out the beamforming process based on the weights to generate an image associated with the scanning.

According to the first aspect and the like of the invention, when an ultrasonic image is generated, weights used in the beamforming process can be calculated from a plurality of transmitted/received signals within the selection range including the direction of the scanning of the ultrasonic wave. An adaptive beam forming process can then be carried out on the basis of the calculated weights, whereby an ultrasonic image having resolution higher than that of an image obtained in related art.

A second aspect of the invention is directed to the image generation apparatus according to the first aspect of the invention, in which the setting of the selection range includes setting the selection range in accordance with a drive condition associated with the scanning.

According to the second aspect of the invention, the selection range can be set in accordance with the drive condition associated with the scanning of the ultrasonic wave.

A third aspect of the invention is directed to the image generation apparatus according to the second aspect of the invention, in which the setting of the selection range according to the drive condition includes setting a narrower selection range when a higher transmission frequency of the ultrasonic wave is used.

According to the third aspect of the invention, a narrower selection range can be set when a higher transmission frequency of the ultrasonic wave is used.

A fourth aspect of the invention is directed to the image generation apparatus according to the second or third aspect of the invention, in which the setting of the selection range according to the drive condition includes setting a narrower selection range when a drive element associated with the scanning has a wider opening width.

According to the fourth aspect of the invention, a narrower selection range can be set when the drive element has a wider opening width.

A fifth aspect of the invention is directed to the image generation apparatus according to any of the first to fourth aspects of the invention, in which the generation of an image is allowed to be accompanied or not by a predetermined harmonic process when an image associated with the scanning is generated, and the setting of the selection range includes setting a narrower selection range in a case where the harmonic imaging process is carried out than in a case where no harmonic imaging process is carried out.

According to the fifth aspect of the invention, a narrower selection range can be set in the case where the harmonic imaging process is carried out than in the case where no harmonic imaging process is carried out.

BRIEF DESCRIPTION OF THE DRAWINGS

Embodiments of the invention will be described with reference to the accompanying drawings, wherein like numbers reference like elements.

DESCRIPTION OF EXEMPLARY EMBODIMENTS

Figure 1:
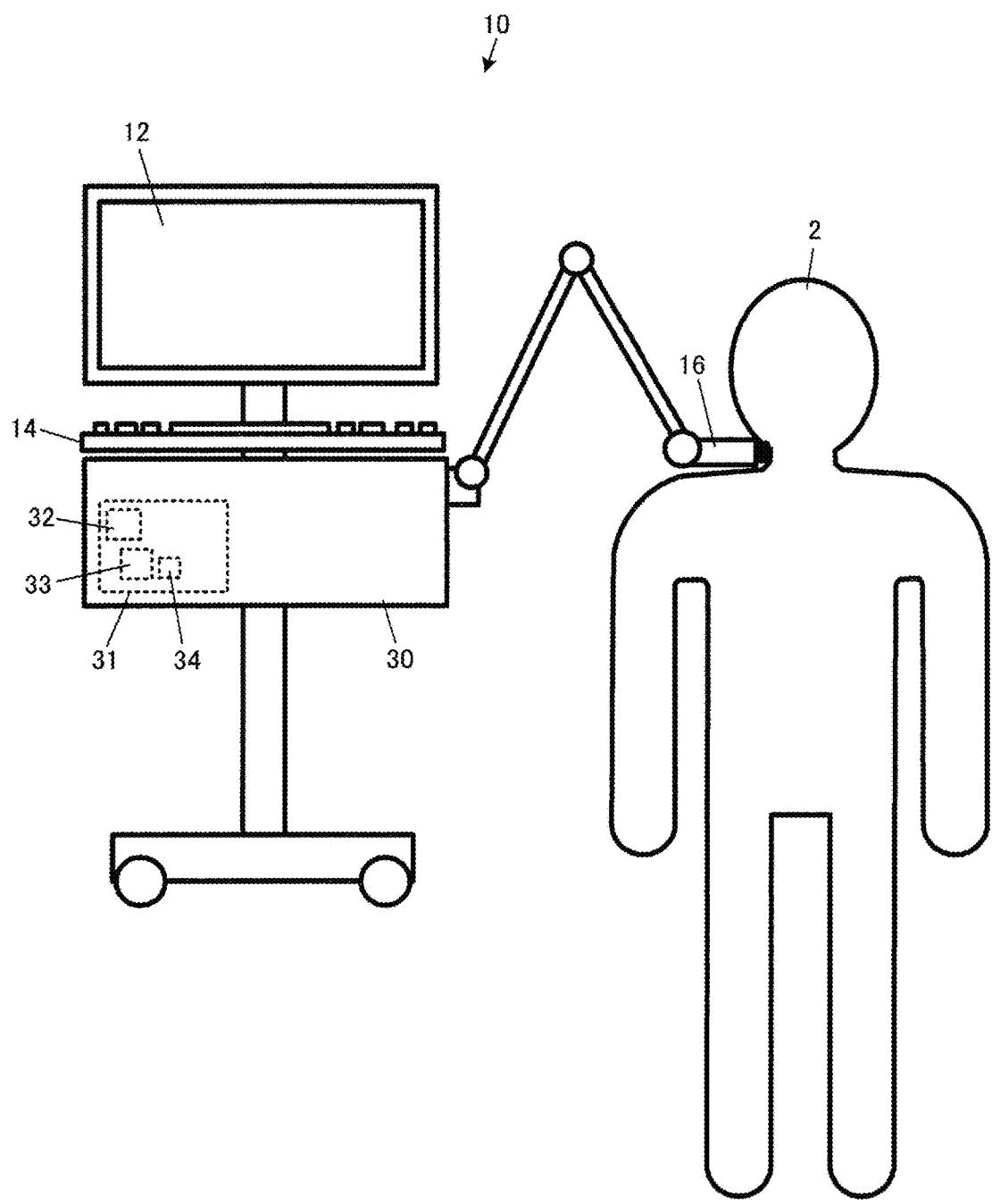
FIG. 1 shows an example of the system configuration of an image generation apparatus.

A preferable embodiment of the invention will be described below with reference to the drawings. The embodiment that will be described below is not intended to limit the invention, and a form to which the invention is applicable is not limited to the following embodiment. Further, in the drawings, the same elements have the same reference characters.

FIG. 1 shows an example of the system configuration of an image generation apparatus 10 in the present embodiment. The image generation apparatus 10 includes a touch panel 12, which serves both as a section for displaying a measurement result and operation information in the form of an image and a section for an inputting operation, a keyboard 14 for the inputting operation, an ultrasonic probe 16, and a processor 30 and acquires biological information on a subject 2 by using ultrasonic measurement.

The processor 30 incorporates a control substrate 31, which is connected to the touch panel 12, the keyboard 14, the ultrasonic probe 16, and other sections of the apparatus so as to be capable of transmitting and receiving signals thereto and therefrom. On the control substrate 31 are mounted a CPU (central processing unit) 32, an ASIC (application specific integrated circuit) 32, an FPGA (field programmable gate array), and a variety of integrated circuits as well as a storage medium 33, such as an IC (integrate circuit) memory and a hard disk drive, and a communication IC 34, which establishes data communication with an external apparatus. The processor 30 causes the CPU 32 or any other component to execute a program stored on the storage medium 33 to carry out processes for acquisition of biological information, such as ultrasonic measurement as a representative example.

Specifically, the image generation apparatus 10 transmits an ultrasonic beam from the ultrasonic probe 16 into the subject 2 and receives a reflected ultrasonic wave for ultrasonic measurement under the control of the processor 30. A signal carrying the received reflected wave is then caused to undergo amplification and signal processing to create reflected wave data containing, for example, positional information on and time-course change in the internal structure of the subject 2. The ultrasonic measurement is repeatedly performed in a predetermined cycle. The measurement unit repeated in the predetermined cycle is called a "frame." The measurement site on which the ultrasonic probe 16 is placed is not limited to a neck region shown in FIG. 1 and may be a region of the subject 2 according to the purpose of the measurement, such as a wrist, an arm, and an abdominal region.

The reflected wave data contains images in the following modes: an A mode; a B mode; an M mode; and a color Doppler mode. The A mode is a mode in which the amplitude of the reflected wave (A-mode image) is displayed with a first axis representing the distance from a predetermined body surface position in the depth direction and a second axis representing the intensity of the signal carrying the received reflected wave. The B mode is a mode in which the amplitude of the reflected wave (A-mode image) produced by scanning a living body with the ultrasonic beam over a predetermined probe scan range (scan angle) is visualized in the form of an image by converting the amplitude into a brightness value and the resultant two-dimensional ultrasonic image (B-mode image) of the internal structure of the living body is displayed.

Principle

Figure 2:
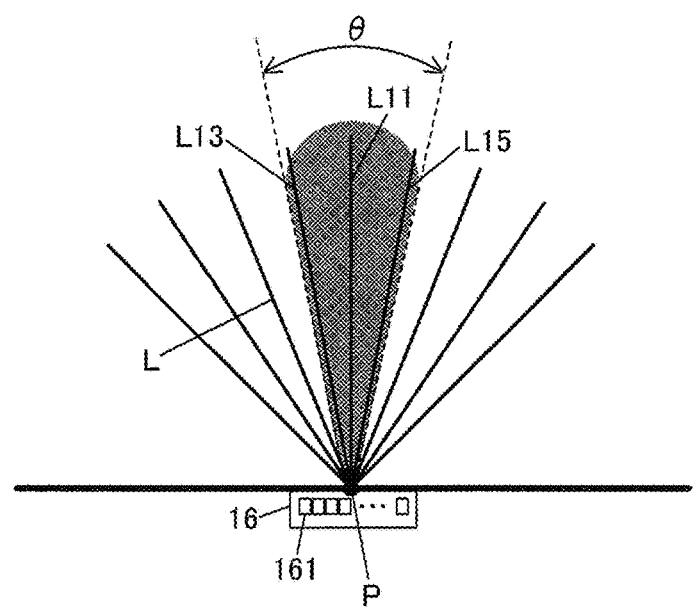
FIG. 2 shows the ultrasonic image.

FIG. 2 shows the ultrasonic image and shows, in a simplified manner, a state in which the ultrasonic probe 16 is placed on a measurement site (body surface) of the subject 2 for the ultrasonic measurement.

The ultrasonic probe 16 has a plurality of built-in ultrasonic elements (ultrasonic vibrators) 161, which are drive elements arranged in a single row or multiple rows. In the present embodiment, the ultrasonic probe 16 will be described as a device that performs ultrasonic measurement in a sector scan scheme, in which an ultrasonic beam is radially transmitted and received along a plurality of scan lines L starting from a base point P in a predetermined body surface position with the angle of incidence of the ultrasonic beam changed by a predetermined angle (scan angle interval) to scan a fan-shaped predetermined angular range, which is a scan angle. The image generation apparatus 10 generates, on the basis of a signal received with each of the ultrasonic elements 161 associated with the scanning along each of the scan lines L, an image according to the scanning along the scan line L. An ultrasonic image is thus obtained.

To generate an image according to each scanning, a beamforming process of summing signals received with the ultrasonic element (hereinafter also simply referred to as "element") 161 associated with the scanning is carried out. In the following sections, the beamforming process in the present embodiment will be described by focusing on a certain scan line (scan line L11 in FIG. 2, for example).

The ultrasonic beam is transmitted so that the acoustic pressure in the direction of a scan line of interest L (scan line of interest L11 to be focused on, for example) by causing each of the elements 161 to operate with a delay period at the time of transmission of the ultrasonic beam (main lobe hatched in FIG. 2). In practice, however, in addition to the ultrasonic beam having the main lobe, low-sensitivity ultrasonic beams (side lobes) are also radiated in oblique directions separate away from the direction of the scan line of interest L11. Further, since an ultrasonic wave is characterized by spreading in a spherical shape, the main lobe itself has a certain width (hereinafter referred to as "main lobe width") θm. Each received signal therefore contains not only a reflected wave (desired wave) from a reflector on the scan line of interest L11 but also a reflected wave (unnecessary wave) from a reflector present in a position separate away from the direction of the scan line of interest. As described above, since an ultrasonic beam is also sensitive to unnecessary waves traveling along directions other than the scan line of interest L11, simply summing signals received with each of the elements 161 causes a problem of degradation in resolution. It is noted that the main lobe in FIG. 2 is intentionally enlarged for ease of understanding, and the size of the main lobe differs in practice from an actual size.

As a technology for solving the problem described above, the MVB process, which is also called adaptive beamforming, has been known. The MVB process, which is a beamforming process carried out with a directional constraint that allows an ultrasonic beam to be sensitive only to a desired wave and prevents the ultrasonic beam from being sensitive to unnecessary waves, allows improvement in resolution.

An overview of the MVB process will be briefly described. In the MVB process, a phasing process is first carried out. The phasing process is a process of delaying a signal received with each of the elements 161 by a pre-specified delay period.

Figure 3:
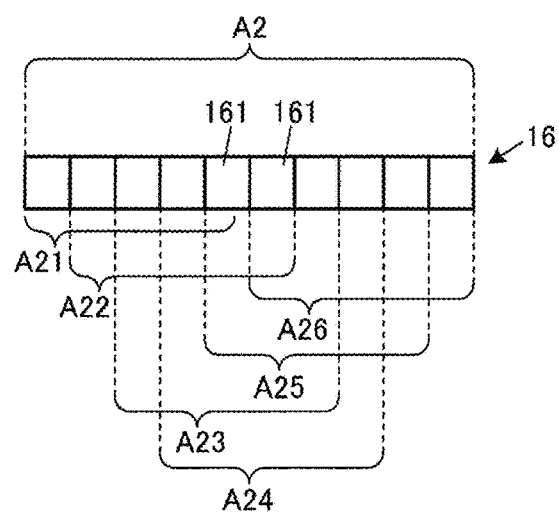
FIG. 3 shows an overview of a spatial averaging process of related art.

Subsequently, a correlation matrix is calculated and used to calculate weights. In the calculation of the correlation matrix, to reduce correlation between a desired wave and an unnecessary wave, a spatial averaging method is applied (spatial averaging process). FIG. 3 shows an overview of the spatial averaging process and shows a simplified element arrangement of the plurality of ultrasonic elements 161, which form the ultrasonic probe 16. The overall width (element opening) A2 of the arranged elements is also referred to as an opening width.

The spatial averaging process is implemented as a process for suppressing the effect of an interference wave (unnecessary wave) that interferes with a desired wave by focusing on the fact that the desired wave and the interference wave correlate with each other. Specifically, the spatial averaging process is a process of calculating correlation matrices from signals received through partial element openings (sub-arrays) A21 to A26 each formed of part of the elements 161, which form the ultrasonic probe 16, and averaging the resultant correlation matrices associated with the sub-arrays A21 to A26 to determine a correlation matrix associated with the overall opening width A2. The spatial averaging process, in which correlation matrices are determined based on the sub-arrays A21 to A26 selectively shifted in the direction in which the sub-arrays are arranged, allows reduction in correlation between the desired wave and the interference wave on the basis of an effect provided by the averaging.

Subsequently, a steering vector $a_\theta$, which is specified on the basis of the direction of the scan line of interest L11, is used to determine weights from the resultant correlation matrix. The calculated weights are then used to perform weighted summation of the signals having been received with the elements 161 and having undergone the phasing process.

The MVB process has, however, the following problem, because the spatial averaging method is applied to the calculation of a correlation matrix. That is, in the spatial averaging process, since a correlation matrix is calculated by using a calculation unit formed of each of the sub-arrays A21 to A26, each of which has an element opening narrower than the actual opening width A2, and weights are then determined, the weighted summation using the calculated weights is also performed by using a summation unit formed of each of the sub-arrays A21 to A26. As a result, the signals received with each of the elements 161 are summed with the element opening thereof narrowed. Improvement in resolution is therefore naturally limited. In other words, if the suppression of the effect of the interference wave and the weighted summation using the summation unit equal to the opening width A1 can be achieved at the same time, the resolution can be further increased.

In view of the consideration described above, to perform the weight calculation, the present embodiment employs a novel method using signals received with the elements 161 associated with the scanning along a plurality of scan lines L including a scan line in the direction of a desired wave. Since part of the contents of the novel process approximates to the MVB process, the novel process is referred to as a "multi-beam MVB process" in the present embodiment. In the following description, the range over which scan lines used in the weight calculation are selected is called a "scan line selection range," and the scan lines in the scan line selection range are called "in-range scan lines." The scan line selection range is an angular range having a center line extending along the direction of the scan line of interest L11, and the in-range scan lines L include at least the scan line of interest L11.

In the multi-beam MVB process, the same phasing process as that in the MVB process is carried out for each of the in-range scan lines L.

The steering vector $a_\theta$ is subsequently calculated. The steering vector $a_\theta$ is expressed by the following Expression (1). In Expression (1), $\theta$ represents a phase shift angle. The phase shift angle $\theta$ corresponds to the angle of the corresponding in-range scan line L (scan line angle $\chi$, which will be described later). M represents the number of elements (number of ultrasonic elements 161). The steering vector $a_\theta$ used in the MVB process described above is fixed to be 1 ($a_\theta=1$, $\theta=0$).

$$a_\theta = (1\, e^{-j\pi\, sin(\theta)}\, e^{-j2\pi\, sin(\theta)} \ldots e^{-j(M-1)\pi\, sin(\theta)}) \tag{1}$$

The steering vector $a_\theta$ is calculated for each of the in-range scan lines L to provide A[n] expressed by the following Expression (2). A[n] is an M×K matrix, and K represents the scan line number of each of the in-range scans line L.

$$A[n] = [a_{\theta_1,n}\, a_{\theta_2,n} \ldots a_{\theta_K,n}] \tag{2}$$

The phase shift process is subsequently carried out. The phase shift process is carried out by determining, in accordance with the following Expression (3), an Hadamard product X~[n] of signals X[n] having been received with the elements 161 for each of the in-range scan lines L and having undergone the phasing process multiplied by A[n] determined by using Expression (2). X~ corresponds to the symbol written in Expression (3) or "X" with "~" labeled thereabove.

$$\tilde{X}[n] = A[n] \circ X[n] \tag{3}$$

X[n] in Expression (3) is expressed by the following Expression (4) and is an M×K matrix, as A[n] is. $x_i[n]$ (i=1, 2, ..., K) represents a signal having been received with each of the elements 161 associated with scanning along the in-range scan line L having the scan line number i and having undergone the phasing process.

$$X[n] = [x_1[n]\, x_2[n] \ldots x_K[n]] \tag{4}$$

The signals X~[n] having been received with the elements 161 for each of the in-range scan lines L and having undergone the phasing process are subsequently used to calculate a correlation matrix R^[n] in accordance with the following Expression (5). R^ corresponds to the symbol written in Expression (5) or "R" with "~" labeled thereabove.

$$\hat{R}[n] = \frac{1}{K}\tilde{X}[n]\tilde{X}[n]^T \qquad (5)$$

The minimization problem shown in the following Expressions (6) and (7) is subsequently solved to calculate a weight w of each of the elements 161.

$$\min_{w} w^T R[n] w, \text{ s.t. } w^T a_{\theta,n} = 1 \qquad (6)$$

$$w = \frac{R^{-1}[n] a_{\theta,n}}{a_{\theta,n}^T R^{-1}[n] a_{\theta,n}} \qquad (7)$$

Thereafter, in accordance with the following Expression (8) and on the basis of the determined weight w of each of the elements 161, signals $x_t\hat{}[n]$ having been received with the elements 161 associated with the scanning along the scan line of interest L11 and having undergone the phase shift process are weighted and summed. The subscript t in Expression (8) represents the scan line number of the scan line of interest L11. $x_t\hat{}$ corresponds to the symbol written in Expression (8) or "$x_L$" with "~" labeled thereabove.

$$|w^T \tilde{x}_t[n]| \qquad (8)$$

In the multi-beam MVB process described above, the correlation between the desired wave and the unnecessary waves can be reduced by using received signals obtained at transmitted beam angles other than that of the scan line of interest L11 as well as the received signal associated with the scan line of interest L11 (observation line). The weighted summation with the effect of the interference wave suppressed can therefore be achieved without narrowing the element opening as in the MVB process of related art but by using a summation unit equal to the opening width A2. In this case, however, choice of the in-range scan lines L (how to set scan line selection range) is an issue to be solved. It is preferable to select at least scan lines L that provide not only a signal intensity roughly equal to that provided by the scan line of interest L11 but also a small amount of variation in the intensity. In view of the above consideration, the resolution is studied in a plurality of simulations in which the main lobe width θm is used as a guideline of the scan line selection range and the scan line selection range is changed so as to be wider and narrower than the main lobe width θm.

First of all, the main lobe width θm is expressed, for example, by the following Expression (9). The main lobe width θm decreases when the transmission frequency f increases and decreases as well when the opening width D increases. In Expression (9), f represents the transmission frequency, D represents the opening width, c represents the speed of sound in a medium, and λ represents the wavelength.

$$\theta = a \sin\{1.02 * c/(f \cdot D)\} \qquad (9)$$

Now, let χ be the angle of a scan line L (scan line angle), and the angular range of the main lobe width θm associated with the scanning along the scan line L ranges from χ−θ/2 to χ+θ/2. Therefore, when the scan line angle χ of each of the scan lines L is expressed by the following Expression (10), the scan lines L within the main lobe can be identified by extraction of the elements in Expression (10) in accordance with the following Expression (11). In Expression (10), α represents the scan angle, and φp represents the scan angle interval. Each of the angles used herein is an azimuth angle and is determined with respect, for example, to the direction corresponding to the angle of incidence of 0°.

$$A = [-\alpha/2, -\alpha/2 + \varphi_P, -\alpha/2 + 2\varphi_P \ldots -\alpha/2] \qquad (10)$$

$$\chi - \theta/2 < A < \chi + \theta/2 \qquad (11)$$

The expression for calculation of the main lobe width θm is not limited to Expression (9). The main lobe width θm, which varies in accordance also with the element shape of the ultrasonic elements 161, whether or not apodization is performed, the distance from the focal position, and other factors, is desirably determined in consideration of the factors described above.

The transmission frequency, which is one of the parameters in Expression (9), which in practice determines the main lobe width θm, is one of conditions under which the ultrasonic probe 16, which is responsible for transmission and reception of an ultrasonic beam, is driven, and the setting of the transmission frequency is changed in accordance, for example, with the depth (distance from ultrasonic probe 16) of an object under observation (also called a region of interest). Specifically, the transmission frequency is set at a large value when a shallow position close to a body surface is observed and set at a small value when a deep position is observed. Since an ultrasonic wave propagating in a living body tends to attenuate in proportion to the transmission frequency, a low frequency, which reduces the amount of attenuation, is used when a deep region is observed, whereas a high frequency, which allows high resolution from the nature of the frequency, is used when a shallow position (shallow region) is observed. The transmission frequency setting described above is performed through the drive condition setting.

Figures 4, 5:
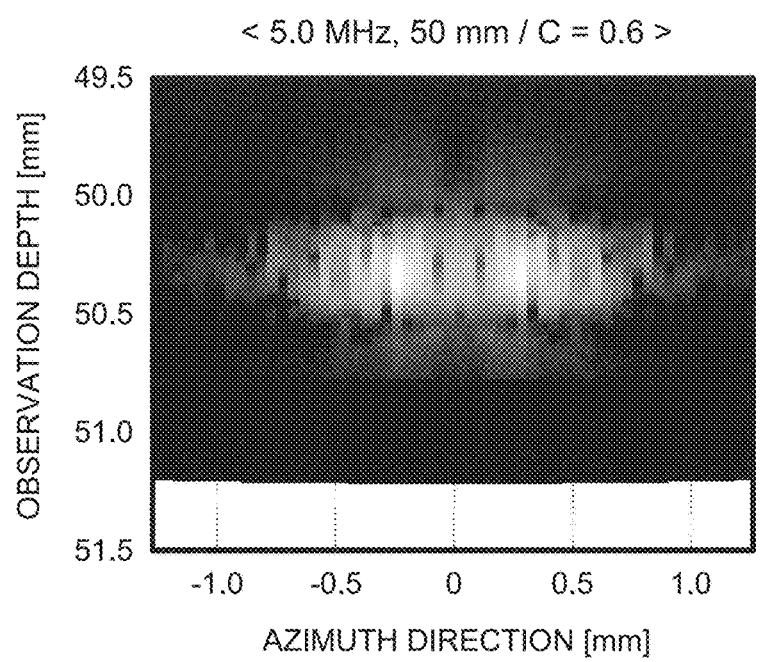
FIG. 4 shows simulation conditions (1) and (2).
FIG. 5 shows an ultrasonic image obtained in the simulation condition (1).

The simulations were performed under the two conditions shown in FIG. 4. First, in a simulation condition (1), the transmission frequency was set at 5.0 MHz assuming a case where a shallow position close to a body surface in a measurement site is observed. The opening width was a fixed value of 19.2 mm, and the scan angle interval was also a fixed value of 0.05°. Scatterers were disposed as an object under observation at a depth level of 50 mm and at intervals of 0.5 mm. Ultrasonic measurement was performed under the above conditions to generate an ultrasonic image.

Next, in the simulation condition (2), the transmission frequency was set at 2.5 MHz assuming a case where a deep region in a measurement site is observed. The opening width and the scan angle interval were the same fixed values as those in the simulation condition (1). Scatterers were disposed as an object under observation at a depth level of 100 mm and at intervals of 3 mm. Ultrasonic measurement was performed under the above conditions to generate an ultrasonic image.

The scan line selection range in the simulations was changed (in-range scan lines L were chosen) by using the following Expression (12), which is a variation of Expression (11), and setting a correction coefficient C as a variable. When C=1.0, the scan line selection range coincides with the main lobe width θm. When C is set at a value smaller than 1.0, the scan line selection range is narrower than the main lobe width θm, and when C is set at a value greater than 1.0, the scan line selection range is wider than the main lobe width θm. For example, consider the scan line of interest L11 in the example shown in FIG. 2. When C=1.0, three scan lines L11, L13, and L15, which fall within the main lobe and include the scan line of interest L11, are chosen.

$$\chi - C*\theta/2 < A < \chi + C*\theta/2 \qquad (12)$$

Figure 6:
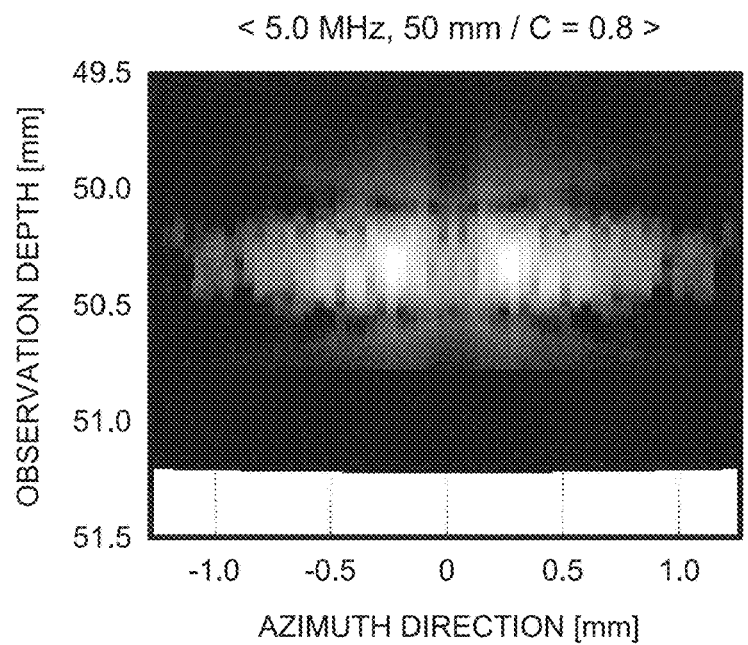
FIG. 6 shows another ultrasonic image obtained in the simulation condition (1).
Figure 7:
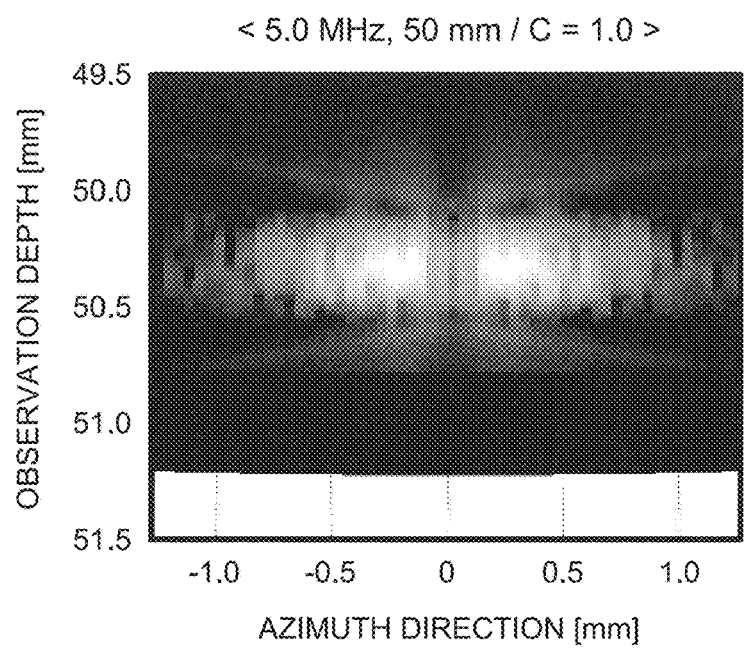
FIG. 7 shows another ultrasonic image obtained in the simulation condition (1).
Figure 8:
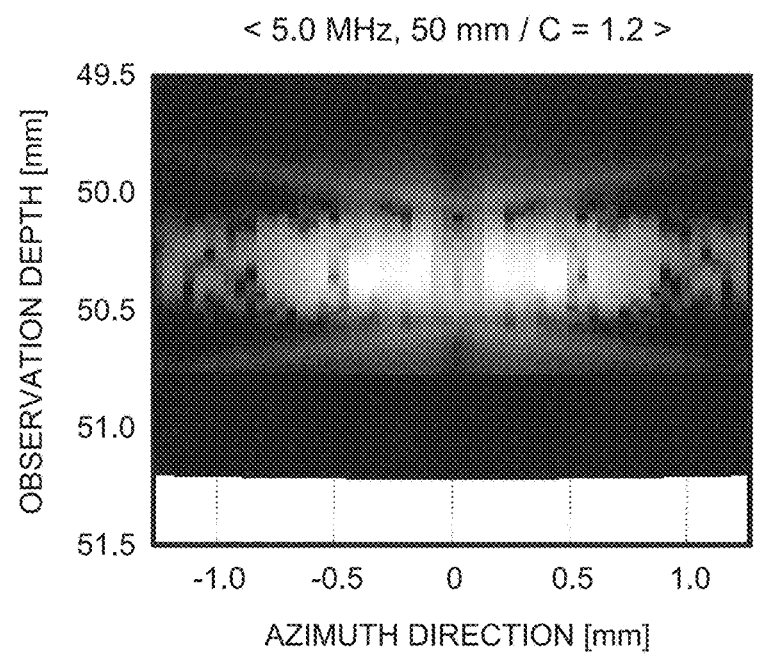
FIG. 8 shows another ultrasonic image obtained in the simulation condition (1).

FIGS. 5 to 8 show ultrasonic images obtained in the simulation condition (1) with the correction coefficient C set at 0.6 in FIG. 5, C=0.8 in FIG. 6, C=1.0 in FIG. 7, and C=1.2 in FIG. 8. FIGS. 9 to 12 show ultrasonic images obtained in the simulation condition (2) with the correction coefficient C set at 0.6 in FIG. 9, C=0.8 in FIG. 10, C=1.0 in FIG. 11, and C=1.2 in FIG. 12.

In both the simulation conditions (1) and (2), when C is set to be smaller than or equal to 1.0, that is, the scan line selection range is set to be narrower than or equal to the main lobe width θm, images showing visible boundaries between the scatterers were obtained, and the resolution was satisfactory. In contrast, in the case where C=1.2 or the scan line selection range was wider than the main lobe width θm, a low-resolution image in which the boundaries between the scatterers were hardly visible and right and left two scatterers were considered to be united to each other was obtained.

Figure 9:
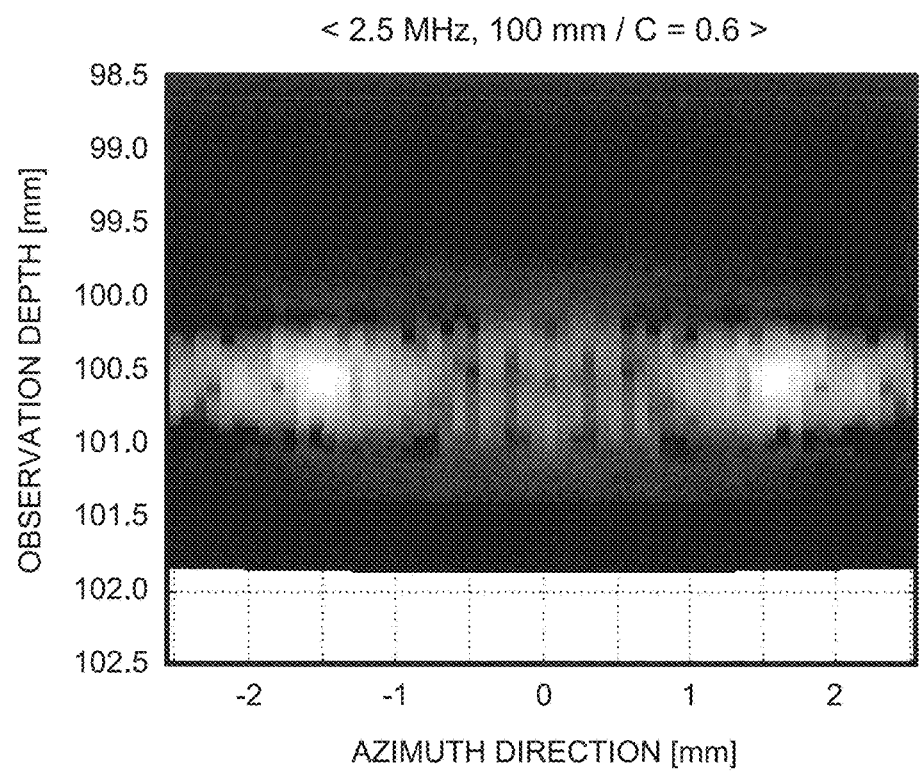
FIG. 9 shows an ultrasonic image obtained in the simulation condition (2).
Figure 10:
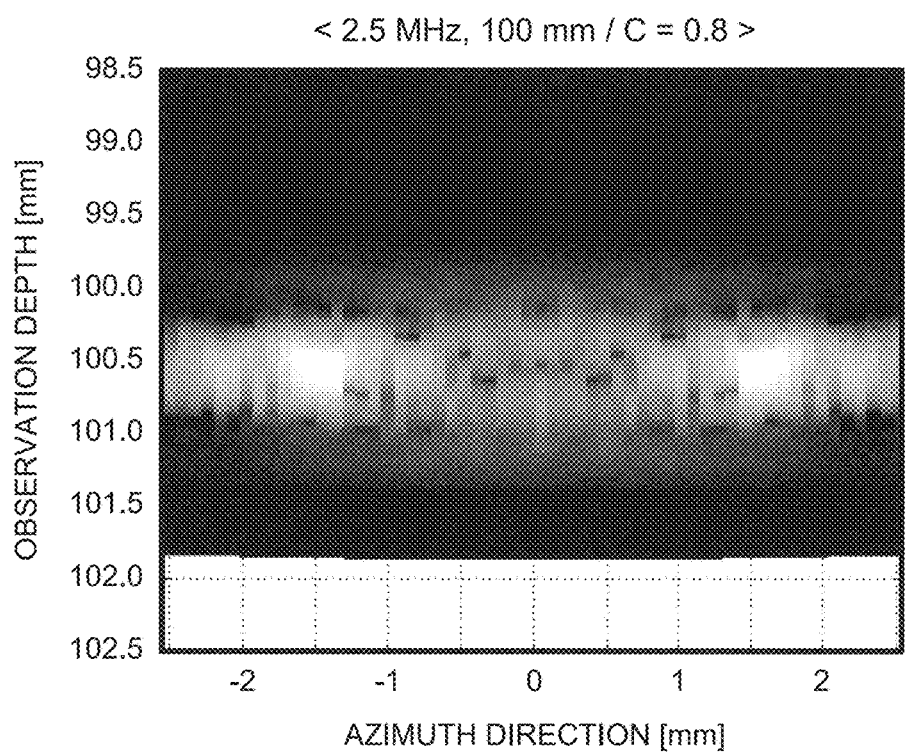
FIG. 10 shows another ultrasonic image obtained in the simulation condition (2).
Figure 11:
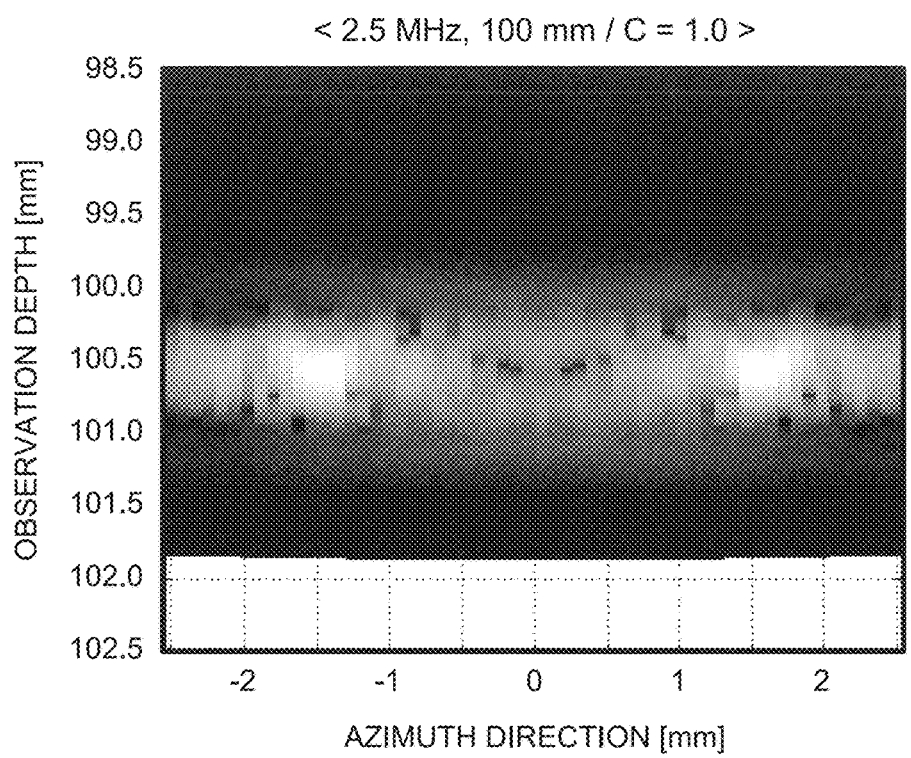
FIG. 11 shows another ultrasonic wave obtained in the simulation condition (2).

Comparison between the results obtained in the simulation condition (1) and the results obtained in the simulation condition (2) shows that the scan line selection ranges are roughly the same angular range in the case where C=1.2 in the simulation condition (1) shown in FIG. 8 and the case where C=0.6 in the simulation condition (2) shown in FIG. 9 because the transmission frequency in the simulation condition (1) (5.0 MHz) is twice the transmission frequency in the simulation condition (2) (2.5 MHz). Comparison between the images in FIGS. 8 and 9 shows that the resolution is satisfactory in the image shown in FIG. 9 because the scan line selection range is narrower than or equal to the main lobe width θm, and that in the image shown in FIG. 8, the resolution is lower than the resolution in the other conditions because the scan line selection range is wider than the main lobe width θm. That is, in the case where the same scan line selection range is set, in which the lower the transmission frequency, the higher the resolution improvement effect, it can be said that with increasing transmission frequency but maintaining the resolution improvement effect requires the scan line selection range to be set at a relatively narrow range.

The ultrasonic probe 16 performs ultrasonic measurement, for example, in a harmonic mode, which is one of ultrasonic measurement modes. The harmonic mode is a mode in which an ultrasonic image is generated by carrying out a harmonic imaging process in which harmonic components (harmonic wave components) are extracted. According to the harmonic imaging process, harmonic wave components produced in the course in which the ultrasonic wave propagates in a living body can be visualized in the form of an image, whereby the resolution and contrast can be improved. An advantageous effect provided by scan line selection range settings in the harmonic mode is also studied.

Figures 12, 13:
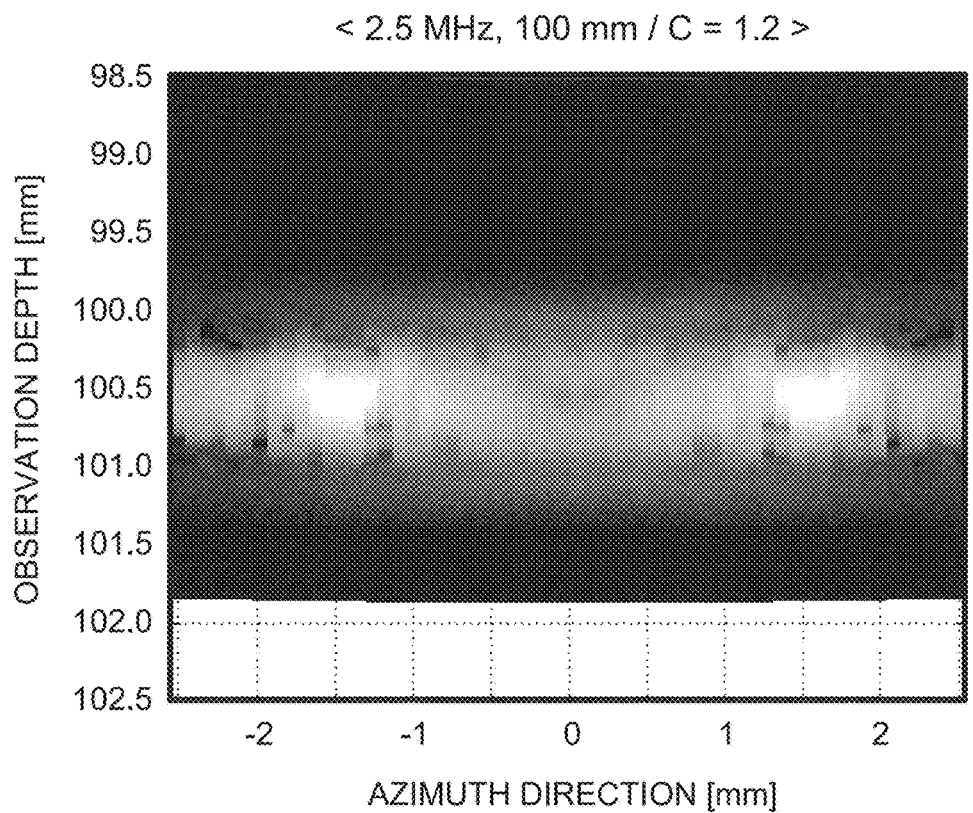
FIG. 12 shows another ultrasonic wave obtained in the simulation condition (2).
FIG. 13 shows conditions under which data are acquired by an actual apparatus when a harmonic mode is selected.

FIG. 13 shows conditions under which data are acquired by an actual apparatus. The harmonic imaging process was carried out by separating a fundamental wave component and harmonic wave components from each other through a frequency filter (high-pass filter) and extracting the second-order harmonic wave component. To this end, the transmission frequency f substituted into Expression (9) in the calculation of the main lobe width θm was not set at 2.6 MHz, which was an actual transmission frequency, but was set at 5.2 MHz, which is twice the actual transmission frequency. Further, as Comparative Example to be compared with the present actual apparatus study, an ultrasonic image was generated by setting the transmission frequency f substituted into Expression (9) at 2.6 MHz, which is the actual transmission frequency. An object under observation was formed of resolution evaluation phantoms (wires) disposed at a depth level of 50 mm and at intervals of 0.5 mm.

Figure 14:
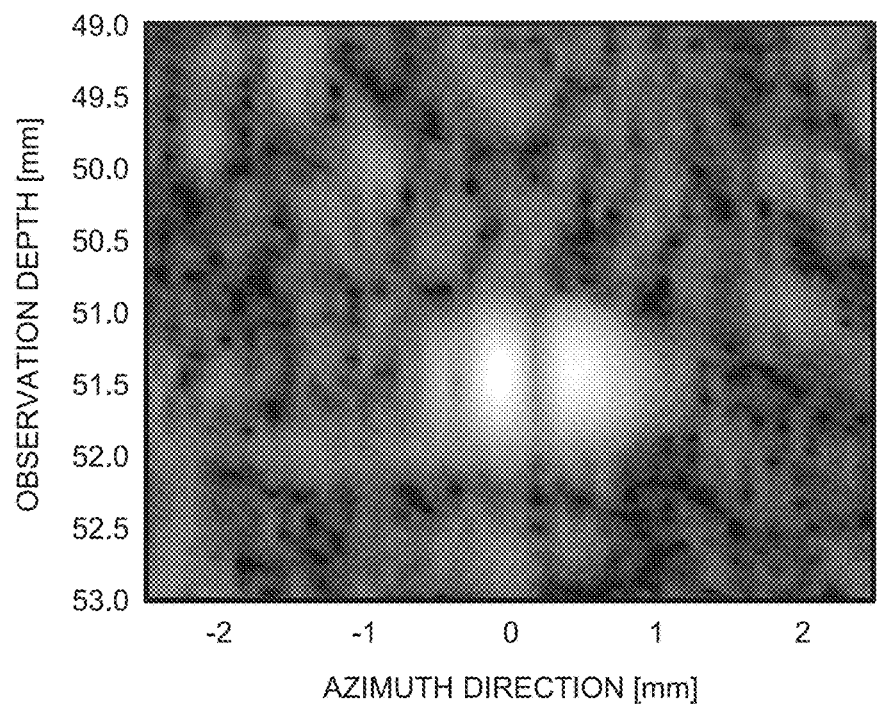
FIG. 14 shows an ultrasonic image obtained in a harmonic wave condition.
Figure 15:
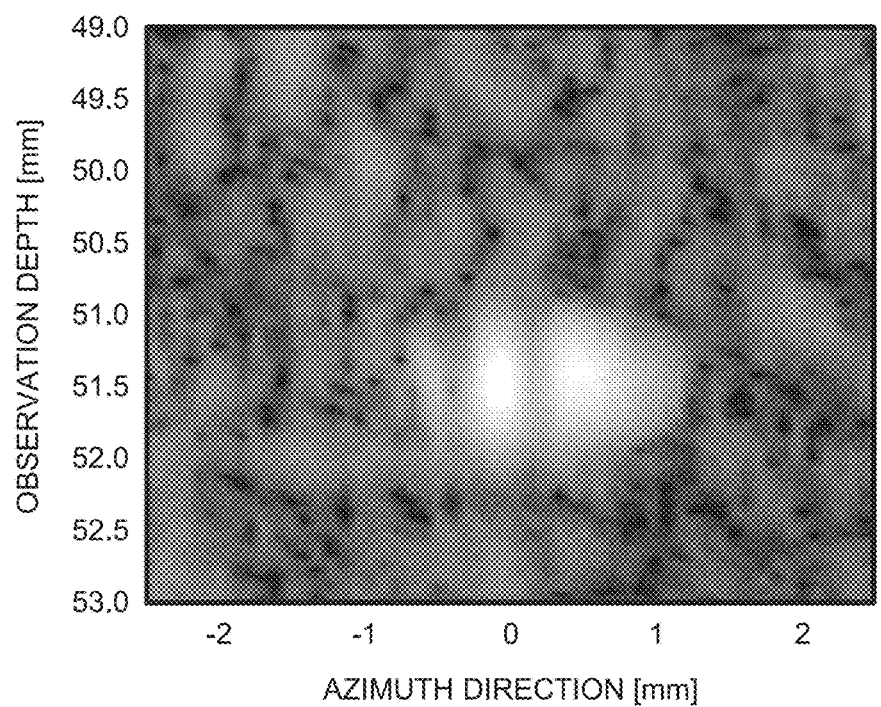
FIG. 15 shows an ultrasonic image obtained in a fundamental wave condition.
Figure 16:
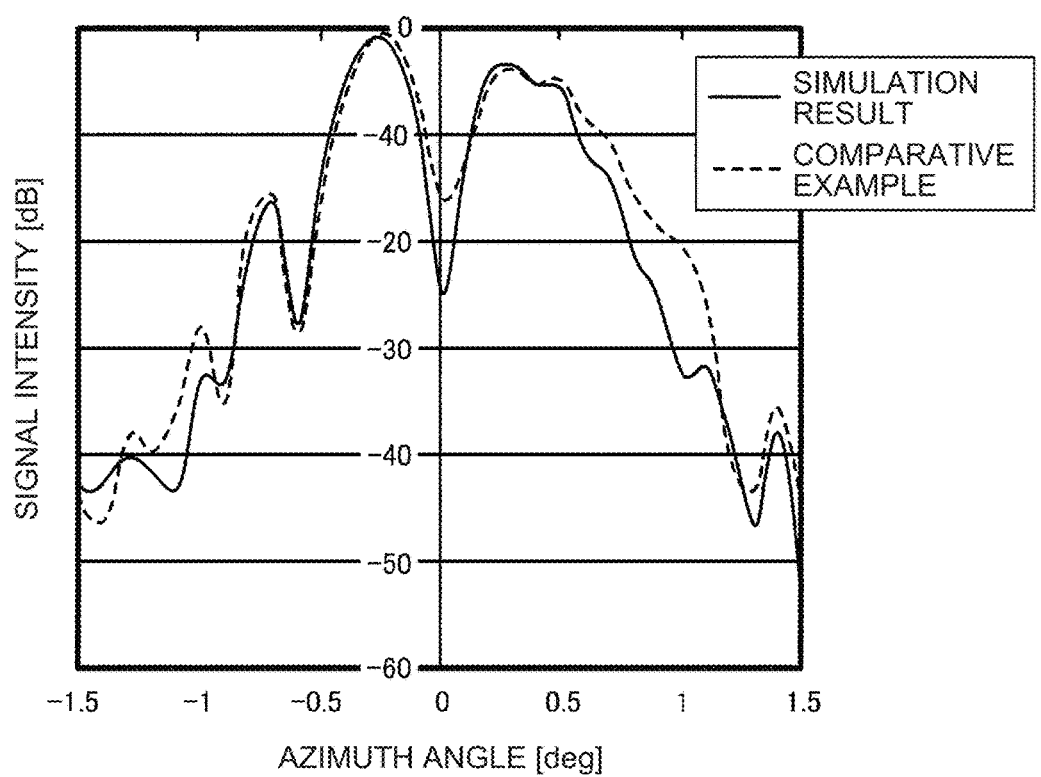
FIG. 16 shows the signal intensity obtained in the harmonic wave condition and the signal intensity in the fundamental wave condition in the form of graphs.

FIG. 14 shows an ultrasonic image obtained in the multi-beam MVB process as an actual apparatus harmonic imaging process under the following conditions: the frequency f is 5.2 MHz; and C=1.0, and FIG. 15 shows an ultrasonic image obtained in the multi-beam MVB process described above under the following conditions: the frequency f is 2.6 MHz; and C=1.0 (fundamental wave condition). Comparison between the two images shows that the image in FIG. 14 (harmonic wave condition) has resolution higher than that of the image in FIG. 15 (fundamental wave condition) in terms of clarity of the boundaries between the resolution evaluation phantoms (wires). FIG. 16 shows both the signal intensity obtained in the harmonic wave condition and the signal intensity obtained in the fundamental wave condition in the form of graphs. The boundary between resolution evaluation phantoms (wires) is located in the direction at an azimuth angle of 0°. Comparison between the harmonic wave condition and the fundamental wave condition in terms of change in the signal intensity on both sides of the azimuth angle of 0° shows that a steeper peak of the signal intensity and hence a higher-resolution image are obtained in the harmonic wave condition than in the fundamental wave condition.

Therefore, in the harmonic mode, it is preferable that the frequency of a harmonic wave component to be extracted is used as a reference and a narrower scan line selection range is set when the frequency is higher.

Functional Configuration

Figure 17:
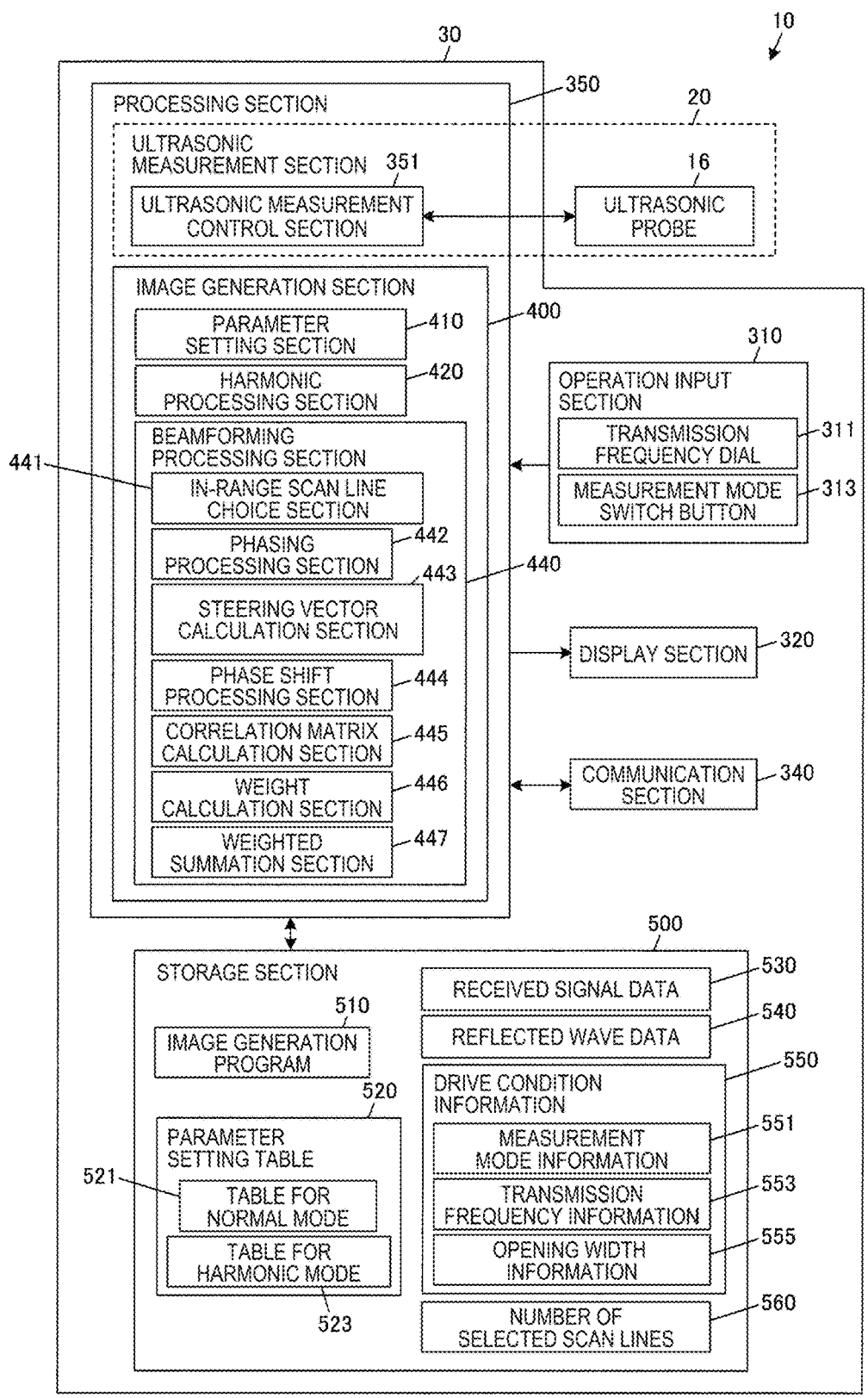
FIG. 17 is a block diagram showing an example of the functional configuration of the image generation apparatus.

FIG. 17 is a block diagram showing an example of the functional configuration of the image generation apparatus 10. The image generation apparatus 10 includes the processor 30 and the ultrasonic probe 16, and the processor 30 includes an operation input section 310, a display section 320, a communication section 340, a processing section 350 as a computation processing section, and a storage section 500.

The ultrasonic probe 16 includes a plurality of ultrasonic elements 161, each of which transmits an ultrasonic wave in response to pulsed voltage outputted from the processor 30 (in more detail, ultrasonic measurement control section 351 in processing section 350). The ultrasonic probe 16 then receives a reflected wave resulting from the transmitted ultrasonic wave and outputs a received signal to the ultrasonic measurement control section 351.

The operation input section 310 accepts a variety of operation inputs from a user and outputs operation input signals according to the operation inputs to the processing section 350. The operation input section 310 can be achieved with a button switch, a lever switch, a dial switch, a trackpad, a mouse, and other components. In FIG. 1, the touch panel 12 and the keyboard 14 correspond to the operation input section 310.

The operation input section 310 has a transmission frequency dial 311 for inputting a transmission frequency indicating value and a measurement mode switch button 313 for selectively switching the measurement mode between a normal mode and the harmonic mode. Each of the transmission frequency dial 311 and the measurement mode switch button 313 is not necessarily achieved by a physical switch, such as a dial switch and a button switch, and may be achieved, for example, by a software-based key switch using a touch panel that also serves as the display section 320. In this case, the user touches and operates the touch panel to input an observation depth indicating value or switch the measurement mode (between normal mode and harmonic mode).

The display section 320 is achieved by a display device, such as an LCD (liquid crystal display) and performs a variety of types of display operation based on a display signal from the processing section 350. In FIG. 1, the touch panel 12 corresponds to the display section 320.

The communication section 340 is a communication device for transmitting and receiving data to and from an external apparatus under the control of the processing section 350. Examples of the communication scheme in accordance with which the communication section 340 operates may include a wired connection scheme via a cable that complies with a predetermined communication standard, a connection scheme via an intermediate device that also serves as a charger called, for example, a cradle, a wireless connection scheme using wireless communication, and a variety of other schemes. In FIG. 1, the communication IC 34 corresponds to the communication section 340.

The processing section 350 is achieved, for example, by a CPU, a GPU (graphics processing unit), and other microprocessors, and an ASIC, a FPGA, an IC memory, and other electronic parts. The processing section 350 controls input and output of data from and to each of the functional sections and carries out a variety of computation processes based, for example, on a predetermined program or data, the operation input signals from the operation input section 310, the signals received with the elements 161 in the ultrasonic probe 16 to acquire biological information on the subject 2. In FIG. 1, the CPU 32 corresponds to the processing section 350. Each section that forms the processing section 350 may instead be formed of hardware, such as a dedicated module circuit.

The processing section 350 includes the ultrasonic measurement control section 351 and an image generation section 400.

The ultrasonic measurement control section 351, along with the ultrasonic probe 16, forms an ultrasonic measurement section 20, which performs ultrasonic measurement. The ultrasonic measurement control section 351 controls the timing at which the ultrasonic probe 16 transmits ultrasonic pulses, produces pulsed voltage at the transmission timing, and outputs the voltage to the ultrasonic probe 16. In this process, a transmission delay process is carried out to adjust the timing at which the pulsed voltage is outputted to each of the elements 161. The ultrasonic measurement control section 351 further filters or otherwise processes signals inputted from the ultrasonic probe 16 and received with the elements 161 and outputs the signals received with the elements 161 and processed (measurement result) are outputted to the image generation section 400.

The image generation section 400 generates an ultrasonic image on the basis of the signals received with the elements 161 and inputted from the ultrasonic measurement control section 351. The image generation section 400 includes the following functional sections: a parameter setting section 410; a harmonic processing section 420; and a beamforming processing section 440. Each of the functional sections may be achieved by software that causes the processing section 350 to execute an image generation program 510 or may be achieved by a dedicated electronic circuit. In the present embodiment, the description will be made with reference to the former case.

The parameter setting section 410 sets drive condition information 550 and the number of selected scan lines 560 on the basis of the dial position of the transmission frequency dial 311 and the selection state of the measurement mode switch button 313.

The harmonic processing section 420 carries out the harmonic imaging process of extracting harmonic components (harmonic wave components) from the signals received with the elements 161 and inputted from the ultrasonic measurement control section 351.

The beamforming processing section 440 is a functional section that carries out the multi-beam MVB process. The beamforming processing section 440 can be divided in correspondence with the steps that form the multi-beam MVB process described above into an in-range scan line choice section 441, which chooses in-range scan lines within a scan line selection range, a phasing processing section 442, which carries out the phasing process, a steering vector calculation section 443, which calculates steering vectors, a phase shift processing section 444, which carries out the phase shift process, a correlation matrix calculation section 445, which calculates a correlation matrix, a weight calculation section 446, which calculates weights, and a weighted summation section 447, which weighs the signals received with the elements 161 by using the weights and sums the weighted signals. The beamforming processing section 440 carries out the beamforming process for each scan line. Each of the functional sections may instead be formed of a dedicated electronic circuit.

The storage section 500 is achieved by a storage medium, such as an IC memory, a hard disk drive, and an optical disk. The storage section 500 stores a program for operating the image generation apparatus 10 and achieving a variety of functions provided by the image generation apparatus 10, data used during the execution of the program, and other pieces of information in advance or temporarily whenever a process is carried out. In FIG. 1, the storage medium 33 mounted on the control substrate 31 corresponds to the storage section 500. The connection between the processing section 350 and the storage section 500 is not limited to connection based on an in-apparatus internal bus circuit and may instead be achieved by a communication line, such as a LAN (local area network) and the Internet. In this case, the storage section 500 may be achieved by an external storage device separate from the image generation apparatus 10.

The storage section 500 stores the image generation program 510, a parameter setting table 520, received signal data 530, reflected wave data 540, the drive condition information 550, and the number of selected scan lines 560.

The processing section 350 reads and executes the image generation program 510 to achieve the functions of the ultrasonic measurement control section 351, the image generation section 400, and other sections. In a case where each of the functional sections is achieved by hardware, such as an electronic circuit, part of the program for achieving the functions can be omitted.

The parameter setting table 520 is referred to when the parameter setting section 410 sets the drive condition information 550 and the number of selected scan lines 560, and the transmission frequency, the scan line selection range, and the number of scan lines are set in advance in accordance with the relationship between the transmission frequency and the scan line selection range described above. The parameter setting table 520 contains a table for the normal mode 521 and a table for the harmonic mode 523. The two tables have the same table structure, have the same ascending/descending tendency of vertically arranged values in the tables shown in FIG. 18, and contain values set in advance suitable for the measurement modes.

Figure 18:
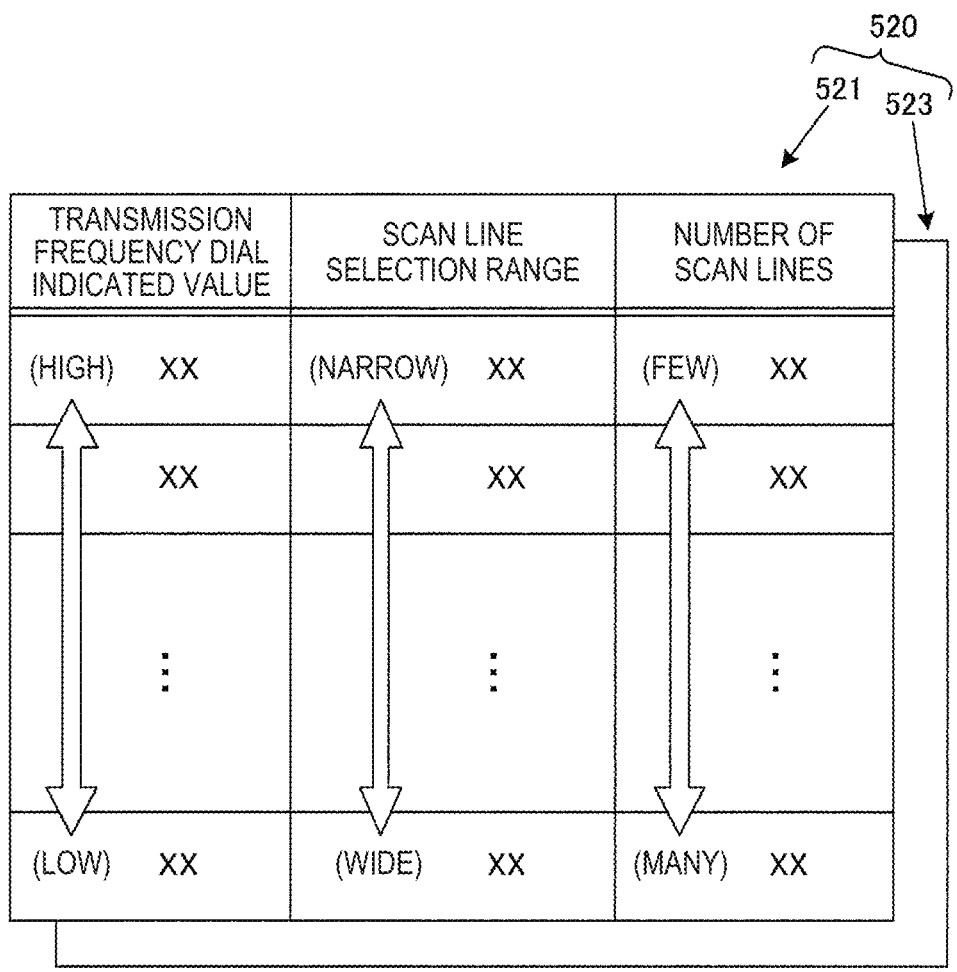
FIG. 18 shows an example of the data configuration of a parameter setting table.

FIG. 18 shows an example of the data configuration of the parameter setting table 520. The parameter setting table 520 is a data table that sets the relationship among a value indicated in the dial position of the transmission frequency dial 311 (transmission frequency dial indicated value), the scan line selection range, and the number of scan lines, as shown in FIG. 18.

In the column of the scan line selection range, the values thereof are set so as to smaller in an upper row where the corresponding transmission frequency is higher, and in the column of the number of scan lines, the number of scan lines within the corresponding scan line selection range is set on the basis of the scan angle interval. In more detail, each value set in the column of the scan line selection range in the table for the normal mode 521 is set, as a precondition, to be smaller than or equal to the main lobe width determined by substitution of the corresponding transmission frequency and opening width (fixed in the present embodiment). On the other hand, each value set in the column of the scan line selection range in the table for the harmonic mode 523 is set to be smaller than or equal to the main lobe width determined by substitution of the frequency of a harmonic wave component specified by the corresponding transmission frequency (for example, the value twice the transmission frequency in a case where the second-order harmonic wave component is extracted) and a fixed opening width.

In the present embodiment, the parameter setting section 410 refers to the parameter setting table 520 and sets, as transmission frequency information 553, a transmission frequency specified by the transmission frequency dial indicated value being selected with the transmission frequency dial 311 and further sets, as the number of selected scan lines 560, the number of scan lines corresponding to the transmission frequency dial indicated value. The in-range scan line choice section 441 then chooses, as the in-range scan lines, scan lines specified in terms of number by the number of selected scan lines 560 and including a scan line of interest of the beamforming process as the center scan line. The scan line selection range is thus set.

The received signal data 530 stores the signals received with the elements 161 associated with scanning along the scan lines and resulting from ultrasonic measurement.

The reflected wave data 540 stores reflected wave data obtained in ultrasonic measurement repeated on a frame basis. The reflected wave data 540 contains data on the B-mode image, which is an ultrasonic image, on a frame basis.

The drive condition information 550 stores measurement mode information 551, transmission frequency information 553, and opening width information 555. The measurement mode information 551 indicates whether the measurement mode being selected with the measurement mode switch button 313 is the normal mode or the harmonic mode. In the transmission frequency information 553, the transmission frequency dial indicated value being selected with the transmission frequency dial 311 is set by the parameter setting section 410, as described above. In the opening width information 555, the opening width A2 (see FIG. 3) of the ultrasonic probe 16 is set in advance as a fixed value.

The stored number of selected scan lines 560 is the number of in-range scan lines within the scan range selection range. The number of selected scan lines 560 is set along with the drive condition information 550 by the parameter setting section 410 before ultrasonic measurement.

Process Procedure

Figure 19:
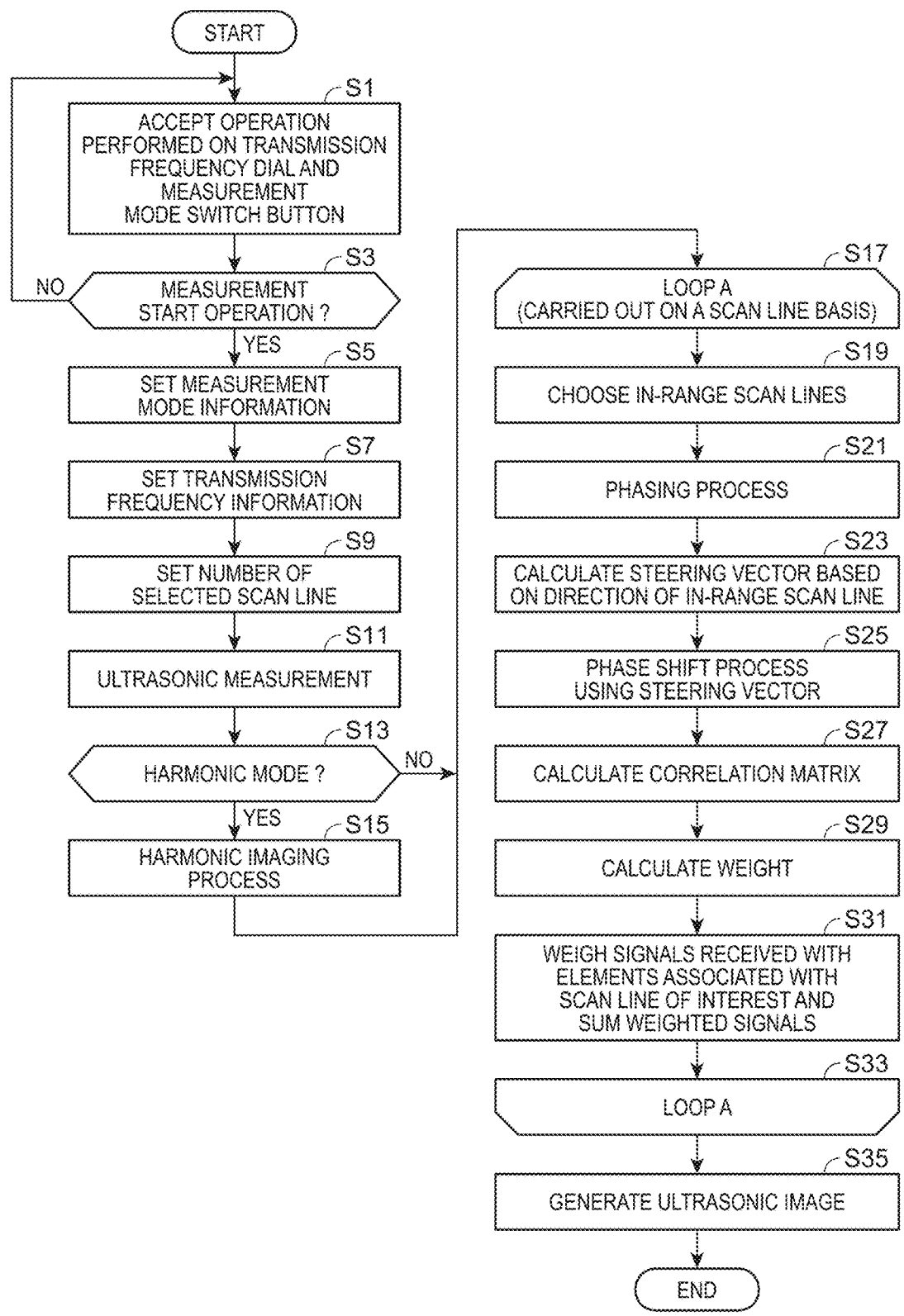
FIG. 19 is a flowchart showing the procedure of the process of generating an ultrasonic image.

FIG. 19 is a flowchart showing the procedure of the process of generating an ultrasonic image in the present embodiment. The process that will be described in this section can be achieved when the processing section 350 reads and executes the image generation program 510 from the storage section 500 and causes the sections in the image generation apparatus 10 to operate. Before ultrasonic measurement, the user puts the ultrasonic probe 16 on a body surface of the subject 2.

The image generation apparatus 10 first accepts the user's operation input performed on the operation input section 310. In this process, the image generation apparatus 10 accepts operation performed on the transmission frequency dial 311 and the measurement mode switch button 313 (step S1) and waits until predetermined measurement start operation is inputted (step S3: NO).

When the measurement start operation is inputted (step S3: YES), the parameter setting section 410 first acquires the selection state of the measurement mode switch button 313 and sets the measurement mode information 551 (step S5). The parameter setting section 410 subsequently sets, on the basis of the dial position of the transmission frequency dial 311, the transmission frequency dial indicated value in the transmission frequency information 553 (step S7). The parameter setting section 410 further reads the number of scan lines corresponding to the transmission frequency dial indicated value indicated by the transmission frequency dial 311 from the parameter setting table 520 and sets the number of selected scan lines 560 (step S9). The transmission frequency information 553 and the number of selected scan lines 560 are set by referring to the table for the normal mode 521 as the parameter setting table 520 when the measurement mode is the normal mode, whereas by referring to the table for the harmonic mode 523 as when the measurement mode is the harmonic mode.

After the drive condition information 550 and the number of selected scan lines 560 are set, the ultrasonic measurement section 20 performs ultrasonic measurement in accordance with the drive condition information 550 (step S11). The process in step S11 allows data corresponding to one frame to be stored in the received signal data 530.

Subsequently, the measurement mode is identified, and in the harmonic mode (step S13: YES), the harmonic processing section 420 causes the received signals obtained in the ultrasonic measurement in step S11 to undergo the harmonic imaging process (step S15).

Subsequently, the beamforming processing section 440 repeats the processes in a loop A on a scan line basis to carry out the multi-beam MVB process (steps S17 to S33). The beamforming processing section 440 first chooses, as the in-range scan lines, scan lines specified in terms of number by the number of selected scan lines 560 and including a scan line of interest of the beamforming process as the center scan line (step S19).

Having chosen the in-range scan lines, the phasing processing section 442 carries out the phasing process of delaying the signal received with the element 161 associated with the scanning along each of the in-range scan lines by a delay period (step S21). In this process, when the measurement mode is the harmonic mode, the phasing is performed on the signal having been received with each of the elements and having undergone the harmonic imaging process in step S15.

The steering vector calculation section 443 then calculates the steering vector specified by Expression (1) for each of the in-range scan lines in accordance with Expression (2) (step S23). The phase shift processing section 444 then uses the steering vector to cause the signals having been received with the elements 161 for each of the in-range scan lines and having undergone the phasing process to undergo the phase shift process in accordance with Expressions (3) and (4) (step S25). The correlation matrix calculation section 445 then calculates a correlation matrix in accordance with Expression (5) from the signals having been received with the elements 161 for each of the in-range scan lines and having undergone the phase shift process (step S27). The weight calculation section 446 then uses the steering vectors and the correlation matrices to calculate weights in accordance with Expressions (6) and (7) (step S29). The weighted summation section 447 then uses the weights determined in step S29 to weigh the signals having been received with the elements 161 for the scan line of interest and having undergone the phase shift process and sums the weighted signals (step S31).

After the processes in the loop A are carried out for all the scan lines of interest, desired processing is performed on each of the resultant images associated with the corresponding scanning to generate an ultrasonic image (step S35). The processes corresponding to one frame is thus completed. The generated ultrasonic image is displayed by the display section 320 as appropriate.

As described above, according to the present embodiment, in-range scan lines within a selected scan lines range are chosen on a scan line basis for the multi-beam MVB process. In this process, a narrower scan line selection range can be set when a higher transmission frequency is used to achieve a high-resolution ultrasonic image. In the setting of the scan line selection range, for example, when a higher transmission frequency is used, a smaller number of scan lines is set as the number of selected scan lines 560 before ultrasonic measurement. The beamforming process can be carried out on a scan line basis by choosing, as the in-range scan lines, scan lines specified by the number of selected scan lines 560 and including a scan line of interest as the center scan line.

In the harmonic mode, with reference to the frequency of a harmonic wave component to be extracted, a narrower scan line selection range can be employed (the number of in-range scan lines can be reduced) when the frequency is higher, whereby the resolution can be further increased, and a high-definition ultrasonic image can be obtained.

In the embodiment described above, the sector scan scheme is presented as an example of the scan scheme of the ultrasonic probe 16. In a case where another scan scheme, such as a linear scan scheme, can be used, the embodiment described above is applicable as well. In the linear scan scheme, ultrasonic beams are transmitted and received along a plurality of scan lines parallel to each other with the positions where the ultrasonic beams are incident shifted along the direction in which the ultrasonic elements 161 are arranged. The setting of the opening width (drive opening) can therefore be changed as required. Therefore, in the case where the linear scan scheme is employed, the scan line selection range may be set (in-range scan lines may be chosen) in accordance with the opening width. In this case, it is preferable to set a narrower scan line selection range (a smaller number of in-range scan lines are chosen) for higher resolution when a wider opening width is used.

Further, even in the case where the sector scan scheme is employed as in the embodiment described above, it is conceivable to perform ultrasonic measurement by changing the ultrasonic probe 16 to another having a different opening width. Assuming such a case, a narrower scan line selection range may be set (a smaller number of in-range scan lines may be chosen) when a wider opening width is used, as in the case where the linear scan scheme is employed. This can be achieved, for example, by preparing parameter setting tables on an opening width basis. Specifically, when values of the scan line selection range corresponding to the same transmission frequency dial indicated value in the parameter setting tables are compared with one another, a narrower scan line selection range and hence a smaller number of scan lines are set when a parameter setting table for a wider opening width is used. The resolution can thus be further increased.

Further, in the embodiment described above, the description has been made with reference to the case where the scan angle interval is fixed. In some cases, the scan angle interval is controlled so as to be, for example, smaller in the vicinity of the center of the scan angle and greater in the vicinity of the ends of the scan angle. In this case, the elements in Expression (10) only need to be set in accordance with the actual scan angle interval. According to the configuration described above, in the beamforming process, the scan line selection range can be set in accordance with the scan angle interval between a scan line of interest and a scan line adjacent thereto.

Further, the procedure of generating an ultrasonic image is not limited to the procedure described with reference to FIG. 19 in which ultrasonic measurement corresponding to one frame is first performed and an image associated with each scanning is then sequentially generated. Instead, the multi-beam process in the loop A may be carried concurrently with the ultrasonic measurement in step S11. In this case, at least after the scanning corresponding to the number of selected scan lines 560 set in step S9 is completed, the process in the loop A may be initiated. According to the configuration described above, a storage area large enough to store received data corresponding to the number of scan lines settable as the number of selected scan lines 560 only needs to be provided, but all received data corresponding to one frame are not required to be stored, whereby the multi-beam MVB process can be carried out with a small amount of memory.

The image generation apparatus according to the embodiment of the invention is not limited to an ultrasonic diagnostic apparatus that performs ultrasonic measurement of the subject 2, as in the embodiment described above, and can be used in a sonar apparatus, an ultrasonic defect inspection apparatus for nondestructive inspection, and other apparatus.

The entire disclosure of Japanese Patent Application No. 2016-054944 filed on Mar. 18, 2016 is expressly incorporated by reference herein.

What is claimed is:
1. An image generation apparatus comprising:
an ultrasonic probe selectively scanning an object by transmitting and receiving an ultrasonic wave; and
a computation processor configured to generate an ultrasonic image from a received signal associated with each scanning in which the ultrasonic wave is transmitted and received,
wherein the computation processor is further configured to:
set, for each scanning, a selection range over which the received signal is received and which includes a direction of the scanning, wherein the selection range indicates a range of scan lines, and the selection range is set based on a main lobe width of a scan line, and wherein the computation processor is con- figured to set the selection range based on a transmission frequency of the ultrasonic wave, calculate weights used in a beamforming process based on the received signals within the selection range, and carry out the beamforming process based on the weights to generate an image associated with the scanning.

2. The image generation apparatus according to claim 1, wherein the setting of the selection range includes decreasing the selection range in response to the transmission frequency of the ultrasonic wave increasing.

3. The image generation apparatus according to claim 1, wherein the setting of the selection range includes decreasing the selection range based on a width of a drive element associated with the scanning.

4. The image generation apparatus according to claim 1, wherein the generation of the image is selectively accompanied by a predetermined harmonic process when an image associated with the scanning is generated, and the setting of the selection range includes setting a narrower selection range in a case where the harmonic imaging process is carried out as compared to a case where no harmonic imaging process is carried out.

5. An image generation method for generating an ultrasonic image from a received signal associated with each scanning of an object in which an ultrasonic wave is transmitted and received, the method comprising:

setting, for each scanning, a selection range over which the received signal is received and which includes a direction of the scanning, wherein the selection range is set based on a transmission frequency of the ultrasonic wave, and wherein the selection range indicates a range of scan lines, and the selection range is set based on a main lobe width of a scan line;

calculating weights used in a beamforming process based on the received signals within the selection range; and carrying out the beamforming process based on the weights to generate an image associated with the scanning.

6. The image generation apparatus according to claim 5, wherein the setting of the selection range includes decreasing the selection range in response to the transmission frequency of the ultrasonic wave increasing.

7. The image generation apparatus according to claim 5, wherein the setting of the selection range includes decreasing the selection range based on a width of a drive element associated with the scanning.

8. The image generation apparatus according to claim 5, wherein the generation of the image is selectively accompanied by a predetermined harmonic process when an image associated with the scanning is generated, and the setting of the selection range includes setting a narrower selection range in a case where the harmonic imaging process is carried out as compared to a case where no harmonic imaging process is carried out.

* * * * *